United States Patent
Glenneberg et al.

[11] Patent Number: 6,153,169
[45] Date of Patent: Nov. 28, 2000

[54] METHOD OF PRODUCING HYDROGEN PEROXIDE AND REACTION PROMOTERS THEREFOR

[75] Inventors: Jürgen Glenneberg, Offenbach; Gustaf Goor, Hanau, both of Germany; Eugen Staab, Mobile, Ala.; Hubert Angert, Hanau, Germany

[73] Assignee: Degussa-Hüls Aktiengesellschaft, Frankfurt am Main, Germany

[21] Appl. No.: 09/175,729

[22] Filed: Oct. 20, 1998

[30] Foreign Application Priority Data

Apr. 11, 1998 [DE] Germany .................. 198 16 297

[51] Int. Cl.⁷ .................................. C01B 15/023
[52] U.S. Cl. ..................... 423/588; 423/589; 423/590
[58] Field of Search ................. 423/588, 589, 423/590

[56] References Cited

U.S. PATENT DOCUMENTS

| | | |
|---|---|---|
| 2,966,397 | 12/1960 | Darbee et al. . |
| 3,923,967 | 12/1975 | Kirchner et al. ............. 423/588 |
| 3,998,937 | 12/1976 | Vaughan ..................... 423/588 |
| 4,374,820 | 2/1983 | Guenter . |
| 5,399,333 | 3/1995 | Kato et al. ................. 423/588 |

FOREIGN PATENT DOCUMENTS

| | | |
|---|---|---|
| 0286610 | 12/1988 | European Pat. Off. . |
| 0453949 | 10/1991 | European Pat. Off. . |
| 0778085 | 6/1997 | European Pat. Off. . |
| 1 112 051 | 8/1961 | Germany . |
| 1 106 737 | 12/1961 | Germany . |
| 1 195 279 | 6/1965 | Germany . |
| 58-180452 | 10/1983 | Germany . |
| 59-51235 | 3/1984 | Japan . |
| 1252822 | 11/1971 | United Kingdom . |

OTHER PUBLICATIONS

Patent Abstracts of Japan entry for Japanese Laid Open Patent Publication No. 58–180452 to Kawasaki KK dated Oct. 21, 1983.

Patent Abstracts of Japan entry for Japanese Laid Open Patent Publication No. 59–51235 to Kawasaki KK dated Mar. 24, 1984.

Ullman's Encyclopedia of Industrial Chem, $5^{th}$ Ed. (1989), vol. 413, 447–457, (No Month).

*Primary Examiner*—Wayne Langel
*Attorney, Agent, or Firm*—Smith Gambrell & Russell, LLP

[57] ABSTRACT

A cyclic anthraquinone process for producing hydrogen peroxide using at least two differently substituted 2-alkylanthraquinones and/or their tetrahydro derivatives. The working solution to be used contains (i) at least one reaction carrier from the series 2-(4-methyl-3-pentenyl) anthraquinone (IHEAQ), 2-(4-methylpentyl) anthraquinone (IHAQ) and their di- and tetrahydro derivatives such as, in particular 2-(4-methylpentyl)-β-tetrahydroanthraquinone (THIHAQ), and (ii) at least one reaction carrier from the series of the 2-($C_1$– to $C_5$)-alkylanthraquinones, especially 2-ethylanthraquinone (EAQ), and their tetrahydro derivatives. The reaction carriers according to (i) make up 5 to 95 molar %, especially 20 to 50 molar % of all reaction carriers. The method is distinguished by greater $H_2O_2$ capacity, improved hydrogenation kinetics and lesser susceptibility to disturbances. A method for making THIHAQ is also disclosed.

22 Claims, No Drawings

6,153,169

METHOD OF PRODUCING HYDROGEN PEROXIDE AND REACTION PROMOTERS THEREFOR

INTRODUCTION AND BACKGROUND

The present invention relates to a method of producing hydrogen peroxide according to the cyclic anthraquinone process. The working solution to be used contains as the reaction carrier at least two differently substituted 2-alkylanthraquinones and/or the corresponding 2-alkyltetrahydroanthraquinones. In another aspect, the present invention relates to a novel reaction carrier.

In the so-called cyclic anthraquinone process for producing hydrogen peroxide, 2-alkylanthraquinones and/or their nuclear-hydrogenated 2-alkyl-$\alpha$- and/or $\beta$-tetrahydroanthraquinones, functioning as reaction carriers, are hydrogenated in an organic solvent system in the presence of a hydrogenating catalyst with hydrogen or a gas containing hydrogen, whereby the reaction carriers are converted at least partially into the hydroquinone form. The solution, containing one or more reaction carriers in the hydrogenated or oxidized form and the organic solvent system, is generally designated as the working solution. After the hydrogenation stage, the working solution is freed from the hydrogenating catalyst and is then treated in the oxidation stage with an oxygen-containing gas, during which the quinone form of the reaction carriers re-forms together with the formation of hydrogen peroxide. After separation of the resulting hydrogen peroxide from the oxidized working solution, customarily done by extraction with water and/or with an aqueous solution containing hydrogen peroxide, the working solution is fed back to the hydrogenation stage. Aside from the cited stages, the process can also include a regeneration of the working solution, in which case anthraquinone derivatives such as anthraquinone epoxides formed in the cyclic process and which are inactive as reaction carriers are re-activated and/or 2-alkyltetrahydroanthraquinones are dehydrogenated to the corresponding 2-alkylanthraquinone derivatives and, as required, even losses of reaction carriers are replaced by the addition of the corresponding 2-substituted anthraquinones and/or their tetrahydro derivatives. A further stage relates to the regeneration of the catalyst in order to maintain a high activity. A survey of the cyclical anthraquinone process is contained in Ullmann's Encyclopedia of Industrial Chemistry, 5$^{th}$ ed. (1989), vol. A13, 447–457 which is relied on and incorporated herein by reference.

High requirements are placed on the reaction carriers in order to assure the highest possible system output in large-scale plants with the lowest possible susceptibility to interruptions and the lowest possible loss of reaction carriers. One of the requirements concerns in particular the highest possible solubility of the reaction carriers in the solvent system both in the quinone form as well as in the hydroquinone form. The solubility of the hydroquinone form is decisive for the maximal $H_2O_2$ equivalent obtainable in constant operation (=g $H_2O_2$ per liter working solution). Further requirements concern the kinetics of hydrogenation and of oxidation; both reactions should take place as rapidly as possible. Since the hydrogenation and the oxidation are often influenced in an opposite manner by a change in the structure of a reaction carrier even a good reaction carrier system consisting of two or more components often represents only a compromise. Important too are the highest possible chemical stability of the reaction carrier in the catalytic hydrogenation, a high oxidation stability with respect to oxygen and hydrogen peroxide, and furthermore, a high stability with respect to acids and/or alkalis as are used in the regeneration. Finally, the reaction carrier should be as insoluble as possible in water, toxicologically harmless and economically available.

According to GB patent 1,252,822 one or more 2-alkylanthraquinones with 2 to 6 carbon atoms in the alkyl group, especially 2-ethyl-, 2-tert.-butyl- and 2-amylanthraquinone can be used in the anthraquinone process for producing hydrogen peroxide. The 2-alkyltetrahydroanthraquinones which form in the hydrogenation stage are also effective.

In the GB patent previously cited, not a single 2-alkylanthraquinone reaction carrier with 6 C atoms in the alkyl group is mentioned by way of example or even emphasized. In EP-A documents 0286610 and 0778085 2-hexenylanthraquinone is cited as a reaction carrier along with other 2-alkylanthraquinones and mixtures. Which of the possible hexenyl isomers is meant and whether or which advantages can be achieved therewith can not be gathered from these EP documents. It is known that as the chain length of the alkyl substituent increases in 2-alkylanthraquinones the quinone solubility increases; however, at the same time, and this is probably more important for practicability, the rate of hydrogenation drops off sharply. Thus, it was not obvious to seriously consider the use of a 2-$C_6$-alkylanthraquinone as a reaction carriers.

It follows from JP-A 58 180452 and JP-A 59 051235 that 2-(4-methyl-3-pentenyl)-1,4-dihydroanthraquinone as well as 2-(4-methyl-3-pentenyl)anthraquinone obtainable therefrom and 2-(4-methylpentyl)anthraquinone can be used as reaction carriers for the production of hydrogen peroxide. The production of the cited compounds—the parent compound is obtained by Diels-Alder reaction from 1,4-naphthoquinone and myrcene—can be gathered from these documents. Concerning the use of these compounds in the cyclical anthraquinone process for the production of hydrogen peroxide, it is solely mentioned that the same results can be obtained as with known 2-alkylanthraquinones.

The requirements placed on a good reaction carrier are occasionally only partly fulfilled when using a single 2-alkylanthraquinone and/or the corresponding 2-alkyltetrahydroanthraquinone, formed in situ, as a function of the operating conditions. Great efforts were therefore undertaken by those in this field of technology to improve the reaction carrier by using at least two different 2-alkylanthraquinones and/or their tetrahydro derivatives. However, advantages regarding the one or the other requirement on a good system of reaction carriers often oppose disadvantages regarding other criteria.

It is possible according to DE-AS 11 95 279 to raise the yield of hydrogen peroxide and/or to minimize the creation of byproducts during the hydrogenation if, instead of using a single 2-alkylanthraquinone such as 2-ethyl-, 2-isopropyl-, 2sec.-butyl- or 2-tert.-butylanthraquinone, an almost eutectic mixture of at least two 2-alkylanthraquinones such as preferably 2-ethyl and 2.-sec.-butylanthraquinones is used in a weight ratio of 27 to 73 and if the degree of hydrogenation is held below 40%. A disadvantage of this method is the necessity of having to limit the degree of hydrogenation. An even more significant disadvantage is the unsatisfactory hydrogenation kinetics of these eutectic mixtures. Similar mixtures of two $C_1$ to $C_4$ alkylanthraquinones, which can be present in the so-called "anthra" system but also the tetra system, are known from U.S. Pat. No. 2,966,397.

U.S. Pat. No. 4,374,820 suggests using a mixture of 2-tert.-butylanthraquinone and 2-sec.-amylanthraquinone including their tetrahydro compounds. This system does have good oxidation kinetics but unsatisfactory hydrogenation kinetics. On the other hand, DE-OS 11 12 051 and 11 06 737 recommend using a mixture of isomeric 2-amylanthraquinones, especially a mixture of 2.-sec.-amyl- and 2-tert.-amylanthraquinone and their tetrahydro derivatives as reaction carriers. A high $H_2O_2$ equivalent can be obtained with such systems on account of their good quinone and hydroquinone solubility; however, the unsatisfactory hydrogenation kinetics are also disadvantageous here, the consequence of which is a poor space-time yield.

Even the use of a reaction carrier system based on 2-ethylanthraquinone (EAQ) and 2-amylanthraquinone (AAQ) and their tetrahydro derivatives (THEAQ and THAAQ) is known—see EP-A 0453949 and Chemical Economics Handbook—SRI International, June 1992, CEH Product Review Hydrogen Peroxide. A reaction carrier system on this basis (EAQ/THEAQ and AAQ/THAAQ) results in comparison to a reaction carrier system based on 2-ethylanthraquinone and 2-ethyl-tetrahydroanthraquinone in an increased $H_2O_2$ equivalent which can also be maintained under operating circulatory conditions. A disadvantage of the reaction carrier system based on EAQ/THEAQ and AAQ/THAAQ is its susceptibility to interruptions in the hydrogenation stage which makes itself noticeable in a reduced take-up of hydrogen. When using a suspension catalyst such as Pd-black this behavior forces the need for a relatively high circulation of hydrogenation catalyst and to further elevate it upon interruptions; however, this lowers the economy of the process.

It is therefore an object of the present invention to produce hydrogen peroxide using a working solution containing at least two differently substituted 2-alkylanthraquinones and/or their tetrahydro compounds which method exhibits to a lesser extent the disadvantages of the methods using the previously known 2-alkylanthraquinone combinations, especially those based on ethyl- and amylanthraquinone and their tetrahydro derivatives.

A further object of the system of the invention is to obtain, given good hydrogenation kinetics, a higher $H_2O_2$ equivalent which can be reliably controlled operationally and it should be less problem-prone.

SUMMARY OF THE INVENTION

The above and other objects of the present invention can be achieved by a method of producing hydrogen peroxide according to the cyclic anthraquinone process, comprising a hydrogenation stage, an oxidation stage and a stage for isolating the hydrogen peroxide using a working solution containing at least two differently substituted 2-alkylanthraquinones and/or their 2-alkyltetrahydro compounds.

A feature of the method of the present invention resides in that a working solution is used which contains (i) at least one reaction carrier selected from the group consisting of 2-(4-methyl-3-pentenyl) anthraquinone (IHEAQ), 2-(4-methylpentyl) anthraquinone (IHAQ) and their nuclear-hydrogenated di- and tetrahydroanthraquinone derivatives and (ii) at least one reaction carrier selected from the group consisting of 2-($C_1$ to $C_5$) alkylanthraquinones and their tetrahydro anthraquinone derivatives, wherein reaction carriers according to (i) are present in an amount of 5 to 95 molar % relative to the sum of all reaction carriers.

DETAILED DESCRIPTION OF INVENTION

The reaction carrier components according to (i) present in accordance with the invention are one or more compounds selected from the group consisting of 2-(4-methyl-3-pentenyl) anthraquinone, also designated subsequently as 2-isohexenylanthraquinone or abbreviated as IHEAQ, 2-(4-methylpentyl) anthraquinone, also designated subsequently as isohexylanthraquinone or abbreviated as IHAQ, 2-(4-methyl-3-pentenyl)-1,4-dihydroanthraquinone (=1,4-dihydro-IHEAQ), 1,2,3,4-tetrahydro-IHAQ (α-THIHAQ), 5,6,7,8-tetrahydro-IHAQ (β-THIHAQ), 5,6,7,8-tetrahydro-IHEAQ (β-THIHEAQ) and intermediate stages of the hydrogenation of IHEAQ and IHAQ to THIHEAQ and/or THIHAQ under conditions of the anthraquinone process.

In the cyclic process primarily β-THIHAQ along with a little α-THIHAQ forms from IHAQ. The abbreviation THIHAQ stands for the isomeric mixture formed in the process.

In the method of the invention especially preferred reaction carriers according to (i) are IHEAQ and IHAQ as well as their β-tetrahydro derivatives, especially β-THIHAQ. As a result of the cyclic anthraquinone process IHAQ and THIHAQ form in the working solution when using IHEAQ as the component according to (i) after fairly long operation.

IHEAQ can be obtained by means of a Diels-Alder reaction from 1,4-naphthoquinone and myrcene and a subsequently introduced, base-catalyzed oxidation of the 1,4, 4a,9a-tetrahydro-IHEAQ with air. IHAQ can be obtained by the hydrogenation of IHEAQ, e.g. on Pt/C. α-THIHAQ can be obtained according to U.S. Pat. No. 1,425,250 by the hydrogenation of 1,4-dihydro-IHEAQ.

A further feature of the invention is also represented by 2-(methylpentyl)-5,6,7,8-tetrahydroanthraquinone (THIHAQ), a previously unknown reaction carrier for the cyclic anthraquinone process. This compound can be obtained by the hydrogenation of IHEAQ with Raney nickel or other hydrogenation catalysts such as Pt, Pd, Rh in metallic or carrier-bound form; it is also produced in the cyclic anthraquinone process from IHAQ and THIHEAQ. β-THIHEAQ can also be obtained by a Diels-Alder reaction from tetrahydronaphthoquinone and myrcene with subsequent base-catalyzed oxidation.

The 2-alkylanthraquinones according to (ii) are one or more anthraquinones selected from the group consisting of 2-methyl-, 2-ethyl-, 2-n-propyl-, 2-iso-propyl-, 2-n-butyl-, 2-sec.-butyl- and 2-tert.-butyl- and 2-iso-sec.-amyl and 2-tert.-amylanthraquinone as well as 2-neopentylanthraquinone and/or their tetrahydro derivatives. The reaction carrier preferably contains 2-ethylanthraquinone (EAQ) and 2-ethyl-tetrahydroanthraquinone (α- and β-THEAQ) with β-THEAQ predominating by far as a rule.

According to a preferred embodiment of the invention, the working solution contains as the reaction carrier essentially a combination of EAQ and IHAQ or IHEAQ with the corresponding tetrahydro compounds THEAQ and THIHAQ and/or THIHEAQ. The invention will be explained further using this system.

It is possible to increase a working solution containing essentially EAQ and THEAQ as reaction carrier with 2-isohexenylanthraquinone (IHEAQ) or isohexylanthraquinone (IHAQ) and/or their tetrahydro derivatives in order to raise the $H_2O_2$ capacity therewith. The molar amount of the sum of the anthraquinone- and tetrahydroanthraquinone derivatives with an isohexenyl- and/or isohexyl group, that is, the products according to (i), is usually between 5 and 95% relative to the sum of all active reaction carriers. During the phase of increasing, the molar amount of products according to (i) can also be below 5%. It is advantageous to adjust the molar amount of anthraquinone derivatives according to (i) to values in a range of 10 to 90%, preferably 20 to 80 molar %, and especially 20 to 50% and to then maintain it since the advantageous action of the combination in accordance with the invention, namely, a raising of the maximal $H_2O_2$ capacity with simultaneously better hydrogenation kinetics in comparison to the closest reaction carrier system, containing EAQ/THEAQ and AAQ/THAAQ is the clearest in this range.

After the addition of 2-isohexenylanthraquinone (IHEAQ) to the working solution the isohexenyl group is hydrogenated in the cyclic process to the isohexyl group. Although IHEAQ is not very oxidation-stable by itself (see example 3), surprisingly, no degradation of the isohexenyl group worthy of mention occurs during the oxidation stage in the cyclic anthraquinone process. The IHEAQ content slowly decreases during the cyclic process, whereas the content of IHAQ and of THIHAQ increases. THIHEAQ also formed at the start to a slight extent and drops back during the further course to values below the detection limit.

According to a preferred embodiment of the method of the invention the ratio of IHAQ to THIHAQ and of EAQ to THEAQ is maintained essentially constant during the cyclic process. To this end a part of the working solution is discharged out of the process and supplied to a known dehydrogenating regeneration stage, during which the tetrahydro derivatives present are dehydrogenated and the anthraquinone system is re-formed. The amount of working solution regenerated in this manner is fed back to the cyclic process. It is advantageous if 40 to 80 molar % of all reaction carrier are present in the tetrahydroanthraquinone form.

It was found that as the amount of reaction carriers of type (i) increases, that is, especially IHAQ, IHEAQ and THIHAQ, relative to the sum of all reaction carriers, the hydroquinone solubility and therewith the maximal production capacity of hydrogen peroxide (g $H_2O_2$/l working solution) are raised. This capacity exceeds those analog systems containing the AAQ/THAAQ system instead of IHAQ/THIHAQ—see examples 4.1 to 4.13. Furthermore, the capacity increases with an increasing amount of tetrahydroanthraquinones. Counter to the previous recognition according to which the hydrogenation kinetics become worse with increasing carbon number in the alkyl group of a reaction carrier, the hydrogenation kinetics of the reaction carriers to be used in accordance with the invention according to (i) with an isohexyl- or isohexenyl substituent are surprisingly considerably better than the hydrogenation kinetics of isomeric 2-amylanthraquinones and 2-amyltetrahydroanthraquinones (AAQ/THAAQ)—see examples 5.1 to 5.6. The extraordinary advantage of the method of the invention is based on the fact that a higher $H_2O_2$ capacity with simultaneously improved hydrogenation kinetics is achieved with the reaction carrier combination in accordance with the invention in comparison to the closest previously known reaction carrier system (EAQ, AAQ and their tetrahydro derivatives).

The reaction carrier system of the invention can be used in any generic methods to produce hydrogen peroxide. In the hydrogenation stage known catalysts such as in particular those based on noble metals like Pd, Pt, Ir, Rh, Ru or mixtures of such noble metals, and Raney catalysts of Ni, Co or Fe can be used. The catalysts can be used as suspension catalysts—e.g. Pd-black or carrier-bound noble metals—or in the form of fixed-bed catalysts. The carrier-suspension- and fixed-bed catalysts are in particular noble metals on an inorganic carrier such as $SiO_2$, $TiO_2$ zeolite, $BaSO_4$, or polysiloxane. Finally, the catalyst can also be located on the surface of a monolithic ceramic carrier or of a honeycombed component with a sufficiently large surface. Common hydrogenation reactors are designed as loop reactors, fixed-bed reactors, mammoth pump reactors as well as reactors with integrated static mixers.

The hydrogenation is generally carried out at a temperature in a range of room temperature to 100° C., especially 45 to 70° C. The hydrogenation pressure is customarily in a range of approximately 100 kPa to 1 MPa, especially 200 kPa to 500 kPa. The hydrogenation is usually operated in such a manner that the hydrogen introduced into the hydrogenation circulation system is completely consumed and the degree of hydrogenation is maintained in a range of 30 to 80%.

The working solution containing the reaction carrier system in accordance with the invention generally contains two or more solvents in order to keep the reaction carrier components in the quinone form and the hydroquinone form in solution. Those solvents and solvent combinations can be considered which are known from previously known cyclic anthraquinone processes. Solvent combinations are especially suitable which contain, in addition to an aromatic benzine (multi alkylated benzene), one or more solvents from the series of secondary alcohols such as diisobutylcarbinol, esters such as methylcyclohexylacetate, phosphoric-acid esters such as tris(2-ethylhexyl) phosphate, tri- and tetraalkylated ureas such as tetrabutyl urea, cyclic ureas, pyrrolidones, carbamates and N-alkylated caprolactams such as N-hexylcaprolactam.

Significant advantages of the method of the invention are: a capacity greater by at least 0.6 g $H_2O_2$ per liter working solution in comparison to the closest previously known method; improved hydrogenation kinetics; a lesser susceptibility to disturbances in continuous operation; and a lesser amount of circulating palladium when using Pd-black as catalyst.

The invention is explained further using the following examples and reference examples.

EXAMPLE 1

Production of 2-(4-methyl-3-pentenyl) anthraquinone (=2-isohexenyl anthraquinone or, abbreviated, IHEAQ):

The production took place analogously to JP-A 59-51235 by a Diels-Alder reaction with subsequent aromatization.

397 g (2.56 moles) myrcene (88%, Aldrich company) were placed in a receiver and 405 g (2.48 moles) 1,4-naphthoquinone (97%) subsequently added. The suspension was agitated 2 h at 100° C. (the exothermic reaction was almost complete after approximately 0.5 h). The reaction mixture, a brown oil, was charged into an ethanolic sodium hydroxide solution (3 l ethanol and 40 g NaOH). The suspension was agitated at 50° C. under the introduction of air for 2 h—at first non-dissolved matter went into solution and finally a reddish yellow precipitate began to precipitate. After having cooled off, the solid matter was removed by suction and washed with 250 ml ice-cooled ethanol. After drying 616 g yellow powder were obtained. HPLC analysis showed an amount of 98.5% area IHEAQ. The 1H-NMR spectrum and the melting point (89–90° C, once recrystallized out of n-heptane) corresponded to IHEAQ.

EXAMPLE 2

Production of 2-(4-methylpentyl)-β-tetrahydroanthraquinone (=β-THIHAQ)

500 g (=1.7 moles) IHEAQ (raw product) dissolved in 3.5 l n-butyl acetate were placed in a 5 l hydrogenation vessel with gassing agitator at 50° C. After purging of the apparatus with nitrogen, 100 g Raney nickel (suspended in 500 ml isopropanol) were charged in and the hydrogenation was then started. After 35 1 take-up of $H_2$ (hydroquinone formation) the take-up of $H_2$ slowed down suddenly. After 30 h, when 88 1 $H_2$ had been taken up, the reaction was stopped. According to HPLC the reaction mixture freed of catalyst and solvent contained in % area: 33% educt (=IHEAQ), 45% 2-(4-methyl-3-pentenyl)-β-tetrahydroanthraquinone (=β-THIHEAQ), 11% 2-(4-methylpentyl) anthraquinone (=IHAQ) and 8% of the desired THIHAQ. In order to remove the alkali compounds entrained with the IHEAQ that was added, the reaction mixture freed of the catalyst was washed with 10% hydrochloric acid, then with aqueous sodium hydrogen carbonate solution and then with water and dried. 437 g of the residue remaining after the removal of the solvent was re-hydrogenated into n-butyl acetate (3 l) isopropanol (0.5 l) in the presence of 100 g Raney nickel. After 27.5 h. when the reaction mixture had taken up 74 l $H_2$ the reaction was terminated. After the catalyst had been filtered off, the reaction mixture was thoroughly oxidized by gassing with air and subsequently concentrated. The precipitate was removed by suction and re-washed with isopropanol and finely recrystallized. 304 g β-THIHAQ were obtained as bright yellow powder: according to HPLC the purity was 99.7% area. The 1H-NMR spectrum corresponded to β-THIHAQ.

EXAMPLE 3

Determination of the oxidation stability of 2-(4-methyl-3-pentenyl) anthraquinone (IHEAQ) (=example 3a) in comparison to 2-ethyl anthraquinone (EAQ) (=example 3b): 0.04 mole of the quinone IHEAQ or EAQ was dissolved in 100 ml 1,2-dichlorobenzene. After the addition of 10 mg azo-bis-isobutyronitrile as radical initiator the mixture was agitated under excess of oxygen at 150° C. with a gassing agitator. After 24 h the quinone content was determined by chromatography. The residual quinone content was 41% for IHEAQ, 90% for EAQ.

In contrast to example 3a IHEAQ is surprisingly not degraded oxidatively more than EAQ under the conditions of the cyclic anthraquinone process for producing hydrogen peroxide, although in the cyclic process IHEAQ is detectable for a long time since it is hydrogenated only slowly to 2-(4-methylpentyl) anthraquinone (IHAQ).

EXAMPLE 4

Determination of the hydroquinone solubility of various mixtures of reaction carriers in different solvent systems. The reaction carriers used and their amounts can be gathered from tables 1 and 2.

Method of determination: A suspension of the appropriate working solution and of a slight amount of freshly precipitated palladium-black was filled into a magnetically agitated, thermostatted double-jacketed vessel equipped with a device for the electronic measuring of turbidity. The mixture was slowly hydrogenated using a gas burette and in addition crystal nuclei in the form of hydroquinone were added in order to avoid an overhydrogenation when approaching the solubility limit. The maximum hydroquinone solubility was reached when a turbidity was registered by the measuring device. The hydrogen taken up at this point in time was converted into $H_2O_2$ equivalents, defined as g $H_2O_2$ per l working solution at 20° C.

Examples 4.1, 4.6, 4.8, 4.9 and 4.12 are systems not in accordance with the invention with the reaction carriers EAQ/THEAQ plus AAQ/THAAQ. Examples in accordance with the invention (4.2 to 4.5, 4.7, 4.10, 4.11 and 4.13) contain the reaction carriers EAQ/THEAQ plus IHAQ/THIHAQ or IHEAQ/THIHAQ. The following abbreviations are used herein: EAQ=2-ethylanthraquinone, THEAQ=tetrahydro-EAQ; AAQ=2-amylanthraquinone with amyl standing for a mixture of 1,2-dimethylpropyl and 1,1-dimethylpropyl (=iso-sec.-and tert.-amyl); IHAQ=2-isohexylanthraquinone, THIHAQ=β-tetrahydro-IHAQ. In example 4.7 IHEAQ was used instead of IHAQ.

Whereas the hydrogenation temperature was 60° C. in examples 4.1 and 4.2, all other examples were carried out at 50° C.

In examples 4.1 to 4.5 a mixture of $C_9/C_{10}$-aromatic benzine (AB) and diisobutylcarbinol (DIBC) was used as solvent in a volumetric ratio of 6:4 and in examples 4.6 and 4.7 a mixture of essentially $C_9/C_{10}$-aromatic benzine and tetrabutyl urea (TBH) was used in a volumetric ratio of 2.5:1.

In examples 4.8 to 4.11 the solvent system consisted of $C_9/C_{10}$-aromatic benzine and tris-(2-ethylhexyl) phosphate (TOP) in a volumetric ratio of 3:1 and in examples 4.12 and 4.13 of essentially the $C_9/C_{10}$-aromatic benzine and tetrabutylurea in a volumetric ratio of 2.5:1. The working solutions of examples 4.8 to 4.13 contained inert breakdown products of the anthraquinones used on account of their longer use in a continuous laboratory system. The working solutions of examples 4.12 and 4.13 contained, depending on the production—use of an operating working solution based on EAQ/THEAQ—a considerably greater number of inert substances than examples 4.8 to 4.11.

TABLE 1

| Example No. | 4.1 | 4.2 | 4.3 | 4.4 | 4.5 | 4.6 | 4.7 |
|---|---|---|---|---|---|---|---|
| Q total (mol/l) | 0.70 | 0.70 | 0.70 | 0.70 | 0.70 | 0.70 | 0.70 |
| EAQ (mol/l) | 0.14 | 0.14 | 0.17 | 0.09 | 0.11 | 0.22 | 0.22 |
| THEAQ (mol/l) | 0.21 | 0.21 | 0.25 | 0.26 | 0.17 | 0.34 | 0.35 |
| AAQ (mol/l) | 0.14 | — | — | — | — | 0.06 | — |
| THAAQ (mol/l) | 0.21 | — | — | — | — | 0.08 | — |
| IHAQ *⁾ (mol/l) | — | 0.14 | 0.11 | 0.09 | 0.17 | — | 10.06**⁾ |
| THIHAQ (mol/l) | — | 0.21 | 0.17 | 0.26 | 0.25 | — | 0.08 |
| $H_2O_2$ equivalent (g $H_2O_2$/l) | 14.3 | 14.8 | 11.9 | 12.4 | 13.0 | 11.7 | 13.7 |

*⁾ the IHAQ used still contained a slight % IHEAQ
**⁾ pure IHEAQ was added instead of IHAQ

TABLE 2

| Example No. | 4.8 | 4.9 | 4.10 | 4.11 | 4.12 | 4.13 |
|---|---|---|---|---|---|---|
| Q total (mol/l) | 0.67 | 0.64 | 0.64 | 0.66 | 0.75 | 0.81 |
| EAQ (mol/l) | 0.12 | 0.12 | 0.12 | 0.11 | 0.20 | 0.21 |
| THEAQ (mol/l) | 0.29 | 0.26 | 0.29 | 0.28 | 0.38 | 0.41 |
| AAQ (mol/l) | 0.13 | 0.09 | — | — | 0.08 | — |
| THAAQ (mol/l) | 0.13 | 0.17 | — | — | 0.09 | — |
| IHAQ *⁾ (mol/l) | — | — | 0.13 | 0.08 | — | 0.10 |
| THIHAQ (mol/l) | — | — | 0.11 | 0.19 | — | 0.09 |

TABLE 2-continued

| Example No. | 4.8 | 4.9 | 4.10 | 4.11 | 4.12 | 4.13 |
|---|---|---|---|---|---|---|
| $H_2O_2$ equivalent (g $H_2O_2$/l) | 11.1 | 11.9 | 12.4 | 12.9 | 12.8 | 14.9 |

*) the IHAQ used still contained a slight % IHEAQ
**) pure IHEAQ was added instead of IHAQ It follows from comparing examples 4.1 with 4.2, 4.6 with 4.7, 4.8 with 4.10, 4.9 with 4.11 and 4.12 with 4.13 that the working solutions containing IHAQ/THIHAQ and IHEAQ/THIHAQ surprisingly result in distinctly greater $H_2O_2$ equivalents than the analogous working solutions containing AAQ/THAAQ. It follows from examples 4.3 to 4.5 that as the molar ratio of the sum of the isohexyl-substituted anthraquinones to the sum of the ethyl-substituted anthraquinones increases, the $H_2O_2$ equivalent increases—the molar ratio rises from 40:60 over 50:50 to 60:40, the $H_2O_2$ equivalent from 11.9 over 12.4 to 13.0 g $H_2O_2$/l.

EXAMPLE 5

The hydrogenation kinetics of different working solutions was investigated. The composition of the anthraquinones and of the solvents used as well as of the rate constants k (mol/l. min) at an $H_2O_2$ equivalent of 10.0 and 12.0 g $H_2O_2$/l follow from the table.

Standard test for hydrogenation kinetics: 100 ml of the working solution and 30 mg Pd-black were dispersed by ultrasound and hydrogenated in a double-jacketed vessel equipped with flow deflectors (baffels) and a gassing agitator at 2000 rpm, 50° C. and an absolute pressure of 0.1 MPa hydrogen. The take-up of hydrogen (Nml) over time was registered. The rate constants k (mol/l·min) of hydrogenation were calculated from the differential take-ups of $H_2$ as a function of the conversion. The hydrogenation kinetics were compared with each other at 0.29 mol conversion, corresponding to an $H_2O_2$ equivalent of the working solution of 10.0 g $H_2O_2$/l and at 0.35 mol conversion, corresponding to an $H_2O_2$ equivalent of 12.0 g $H_2O_2$/l. The higher the k, the more rapidly the hydrogenation takes place.

TABLE 3

| Solvent | AB/DIBC (60:40) | | AB/TOP (3:1) | | AB/TOP (3:1) | |
|---|---|---|---|---|---|---|
| Example No. | 5.1 | 5.2 | 5.3 *) | 5.4 *) | 5.5 **) | 5.6 **) |
| EAQ (mol/l) | 0.14 | 0.14 | 0.11 | 0.11 | — | — |
| THEAQ (mol/l) | 0.21 | 0.21 | 0.26 | 0.29 | 0.21 | 0.21 |
| AAQ (mol/l) | 0.14 | — | 0.13 | — | — | — |
| THAAQ (mol/l) | 0.21 | — | 0.12 | — | 0.21 | — |
| IHAQ (mol/l) | — | 0.14 | — | 0.13 | | |
| THIHAQ (mol/l) | — | 0.21 | — | 0.12 | — | 0.21 |
| k · 10⁴ at 10.0 g $H_2O_2$/l | 115 | 121 | 98 | 106 | 310 | 370 |

TABLE 3-continued

| Solvent | AB/DIBC (60:40) | | AB/TOP (3:1) | | AB/TOP (3:1) | |
|---|---|---|---|---|---|---|
| Example No. | 5.1 | 5.2 | 5.3 *) | 5.4 *) | 5.5 **) | 5.6 **) |
| k · 10⁴ at 12.0 g $H_2O_2$/l | 86 | 101 | 60 | 75 | 150 | 240 |

*) The working solutions of examples 5.3 and 5.4 stemmed from a laboratory test system operated for several months and accordingly contained additional inert components from the reaction carrier.
**) A Pd with greater activity than in examples 5.1 to 5.4 was used in the measuring.

The comparative tests (5.1, 5.3 and 5.5 are not in accordance with the invention) show that reaction carrier systems in accordance with the invention permit a more rapid hydrogenation than previously known systems do. The combination EAQ/THEAQ with IHAQ/THIHAQ hydrogenates more rapidly than the combination EAQ/THEAQ with AAQ/THAAQ (compare examples 5.2 with 5.1)—this difference becomes especially clear at an $H_2O_2$ equivalent of 12 g/l.

EXAMPLE 6

A working solution consisting of 75% by volume aromatic benzine ($C_9/C_{10}$-alkyl aromatic mixture), 25% by volume tris (2-ethylhexylphosphate), 0.11 mol/l 2-ethylanthraquinone, 0.29 mol/l 2-ethyltetrahydroanthraquinone, 0.13 mol/l 2-isohexylanthraquinone and 0.12 mol/l 2-isohexyltetrahydroanthraquinone was tested in a test system for the cyclic process of the anthraquinone method for producing hydrogen peroxide, consisting of the method steps of hydrogenation, oxidation, and extraction as well as of drying, regeneration and purification concerning the maximum $H_2O_2$ production capacity obtainable in continuous operation (g $H_2O_2$ produced per liter working solution). The hydrogenation stage (loop reactor) was operated at a hydrogen pressure of 0.35 MPa and a temperature of 58° C. Pd-black (0.5 to 1 g/l) was used as hydrogenation catalyst. The $H_2O_2$ equivalent in the hydrogenation was raised successively to a value of 13.0 g/l and maintained constant for several days without a crystallizing out of hydroquinones being able to be observed. Upon the attempt to raise the capacity to 13.5 g/l hydroquinone crystallized out. Accordingly, the maximum $H_2O_2$ capacity of this working solution is between 13.0 and 13.5 g/l.

EXAMPLE 7
(not in accordance with the invention)

The maximum $H_2O_2$ capacity of a working solution consisting of 75% by volume aromatic benzine ($C_9/C_{10}$-alkyl aromatic mixture), 25% by volume tris (2-ethylhexyl) phosphate, 0.12 mol/l 2-ethylanthraquinone, 0.28 mol/l 2-ethyltetrahydroanthraquinone, 0.13 mol/l 2-amylanthraquinone and 0.12 mol/l 2-amyltetrahydroanthraquinone was determined analogously to example 6. In comparison to example 6 a distinctly greater amount of Pd-black mercury sulfide was necessary here, namely, 2 to 3 g/l, to maintain the hydrogenation in the sense of a complete conversion of the hydrogen used. The maximum $H_2O_2$ of this working solution was below 12.4 g $H_2O_2$/l. A raising of the $H_2O_2$ equivalent above 12.4 resulted in a precipitation of the hydroquinones.

EXAMPLE 8

The maximum $H_2O_2$ capacity of a working solution whose solvent system was based essentially on a $C_9/C_{10}$- aromatic benzine and tetrabutylurea (volumetric ratio AB:TBH approximately 3:1) was determined analogously to example 6 at a hydrogenation temperature of 60° C. The working solution contained as reaction carriers 0.20 mol/l 2-ethylanthraquinone, 0.35 mol/l 2-ethyltetrahydroanthraquinone, 0.09 mole/l 2-isohexylanthraquinone (IHAQ), which still contained some 2-isohexenylanthraquinone (IHEAQ), and 0.07 mol/l 2-isohexyltetrahydroanthraquinone (THIHAQ). The catalyst amount was 0.5 to 1.0 g Pd-black per liter. The maximum $H_2O_2$ capacity was approximately at least 14 g $H_2O_2$/l. An increase was not possible only because the test system did not permit higher $H_2$ feed.

Further variations and modifications of the invention will be apparent to those skilled in the art from the foregoing and are intended to be encompassed by the claims appended hereto.

German priority application 198 16 297.9 is relied on and incorporated herein by reference.

We claim:

1. A method of producing hydrogen peroxide according to a continuous anthraquinone process, comprising:
   hydrogenating a working solution which comprises:
   (i) at least one reaction carrier selected from the group consisting of 2-(4-methyl-3-pentenyl) anthraquinone, di-and tetra-hydroanthroquinone derivatives thereof, 2-(4-methylpentyl) anthraquinone, and di-and tetra-hydroanthroquinone derivatives thereof, and
   (ii) at least one reaction carrier selected from the group consisting of 2-alkylanthraquinones and tetrahydroanthraquinone derivatives thereof, wherein the alkyl substituent of the 2-alkylanthraquinone is an alkyl substituent having from 1 to 5 carbon atoms;
   oxidating the hydrogenated working solution to produce hydrogen peroxide; and
   isolating the hydrogen peroxide,
   wherein the at least one reaction carrier according to (i) is present in an amount from 5 to 95 molar % relative to a total amount of reaction carriers.

2. The method according to claim 1, wherein the at least one reaction carrier according to (ii) is at least one member selected from the group consisting of 2-ethylanthraquinone and 2-ethyltetrahydroanthraquinone.

3. The method according to claim 1, wherein the at least one reaction carrier according to (i) is at least one member selected from the group consisting of 2-(4-methylpentyl) anthraquinone and tetrahydroanthraquinone derivatives thereof, and 2-(4-methyl-3-pentenyl) anthraquinone and tetrahydroanthraquinone derivatives thereof.

4. The method according to claim 1, wherein the at least one reaction carrier according to (i) is at least one member selected from the group consisting of 2-(4-methylpentyl) anthraquinone, 2-(4-methyl-3-pentenyl) anthraquinone, and 5, 6, 7, 8-tetrahydro-2-(4-methylpentyl) anthraquinone.

5. The method according to claim 2, wherein the at least one reaction carrier according to (i) is at least one member selected from the group consisting of 2-(4-methylpentyl) anthraquinone and tetrahydroanthraquinone derivatives thereof, and 2-(4-methyl-3-pentenyl) anthraquinone and tetrahydroanthraquinone derivatives thereof.

6. The method according to claim 2, wherein the at least one reaction carrier according to (i) is at least one member selected from the group consisting of 2-(4-methylpentyl) anthraquinone, 2-(4-methyl-3-pentenyl) anthraquinone, and 5, 6, 7, 8-tetrahydro-2-(4-methylpentyl) anthraquinone.

7. The method according to claim 1, wherein the at least one reaction carrier according to (i) is present in an amount from 10 to 90 molar %, relative to the total amount of reaction carriers.

8. The method according to claim 1, wherein the at least one reaction carrier according to (i) is present in an amount from 20 to 80 molar %, relative to the total amount of reaction carriers.

9. The method according to claim 1, wherein the at least one reaction carrier according to (i) is present in an amount from 20 to 50 molar %, relative to the total amount of reaction carriers.

10. The method according to claim 2, wherein the at least one reaction carrier according to (i) is present in an amount from 10 to 90 molar %, relative to the total amount of reaction carriers.

11. The method according to claim 2, wherein the at least one reaction carrier according to (i) is present in an amount from 20 to 80 molar %, relative to the total amount of reaction carriers.

12. The method according to claim 2, wherein the at least one reaction carrier according to (i) is present in an amount from 20 to 50 molar %, relative to the total amount of reaction carriers.

13. The method according to claim 3, wherein the at least one reaction carrier according to (i) is present in an amount from 10 to 90 molar %, relative to the total amount of reaction carriers.

14. The method according to claim 3, wherein the at least one reaction carrier according to (i) is present in an amount from 20 to 80 molar %, relative to the total amount of reaction carriers.

15. The method according to claim 3, wherein the at least one reaction carrier according to (i) is present in an amount from 20 to 50 molar %, relative to the total amount of reaction carriers.

16. The method according to claim 1, further including the step of providing a further amount of the working solution including at least one member selected from the group consisting of 2-(4-methyl-3-pentenyl) anthraquinone and tetrahydro derivatives thereof, and 2-(4-methylpentyl) anthraquinone and tetrahydro derivatives thereof, in order to maintain the continuous anthraquinone process.

17. The method according to claim 2, further including the step of providing a further amount of the working solution including at least one member selected from the group consisting of 2-(4-methyl-3-pentenyl) anthraquinone and tetrahydro derivatives thereof, and 2-(4-methylpentyl) anthraquinone and tetrahydro derivatives thereof, in order to maintain the continuous anthraquinone process.

18. The method according to claim 1, wherein the reaction carriers comprise from 5 to 95% in the anthroquinone form and from 5 to 95% in the tetrahydroanthraquinone form.

19. The method according to claim 1, wherein the reaction carriers comprise from 20 to 60% in the anthroquinone form and from 5 to 95% in a tetrahydroanthraquinone form.

20. The method according to claim 1, wherein the reaction carriers comprise from 5 to 95% in the anthroquinone form and from 40 to 80% in the tetrahydroanthraquinone form.

21. The method according to claim 1, wherein the hydrogenating takes place in the presence of at least one member selected from the group consisting of a noble-metal suspension catalyst and a carrier-bound noble-metal suspension catalyst.

22. The method according to claim 21, wherein the noble-metal suspension catalyst comprises palladium-black.

* * * * *